United States Patent [19]

Kiang et al.

[11] Patent Number: 4,732,672

[45] Date of Patent: Mar. 22, 1988

[54] UNIVERSALLY APPLICABLE MOUNTING APPARATUS FOR HIGH PRESSURE LIQUID CHROMATOGRAPHY COLUMNS

[76] Inventors: Chih-Hen Kiang; George J. Lee, both of P.O. Box 361932, Milpitas, Calif. 95035-1596

[21] Appl. No.: 30,676

[22] Filed: Mar. 26, 1987

[51] Int. Cl.$^4$ .............................................. B01D 15/08
[52] U.S. Cl. .................................. 210/198.2; 210/249; 210/541; 248/188.4; 248/200.1; 422/70; 422/104
[58] Field of Search ........................... 248/188.4, 200.1; 422/70, 99, 104; 210/198.2, 232, 238, 249, 250, 541, 542

[56] References Cited

U.S. PATENT DOCUMENTS

| | | | |
|---|---|---|---|
| 3,544,281 | 12/1970 | Phillips | 422/104 |
| 3,822,850 | 7/1974 | Elias | 248/200.1 |
| 3,893,813 | 7/1975 | Johnson | 422/104 |
| 4,064,737 | 12/1977 | Sieverin | 422/104 |
| 4,335,872 | 6/1982 | Caplis | 211/60.1 |
| 4,353,869 | 10/1982 | Guth | 422/104 |
| 4,418,040 | 11/1983 | Karamian | 422/104 |
| 4,469,660 | 9/1984 | Jones | 211/41 |
| 4,478,715 | 10/1984 | Goodnight | 210/198.2 |
| 4,550,594 | 11/1985 | Engstrom | 210/198.2 |
| 4,582,204 | 4/1986 | Wright | 211/133 |

Primary Examiner—Ernest G. Therkorn
Attorney, Agent, or Firm—John J. Leavitt

[57] ABSTRACT

Presented is a universally and quickly applicable mounting apparatus for high pressure liquid chromatography columns, providing for supporting and quickly connecting and disconnecting a chromatography column to a solvent line, with the capability of ensuring leak-proof seals at high pressures, and minimizing or reducing to zero the fluid "dead" volume in the connections. The quick-connect and quick-disconnect mounting apparatus works with either male or female column connection unions of both low dead volume and zero dead volume design, does not require the use of tools, and applies pressure uniformly to the upper and lower seals of the column. The apparatus also provides for mounting a sample injector in close proximity to the column inlet to minimize sample dilution and delay. Additionally, the apparatus provides for the quick mounting, and dismounting, without use of tools, of an auxiliary filter device of relatively low cost in comparison to the cost of the column, thus providing for increased longevity of the primary column at maximum efficiency.

19 Claims, 13 Drawing Figures

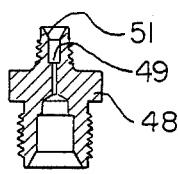 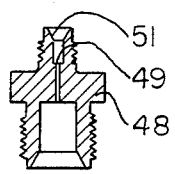 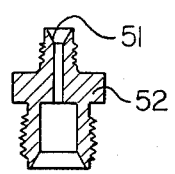 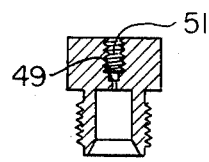
FIG. 7  FIG. 8  FIG. 9  FIG. 10
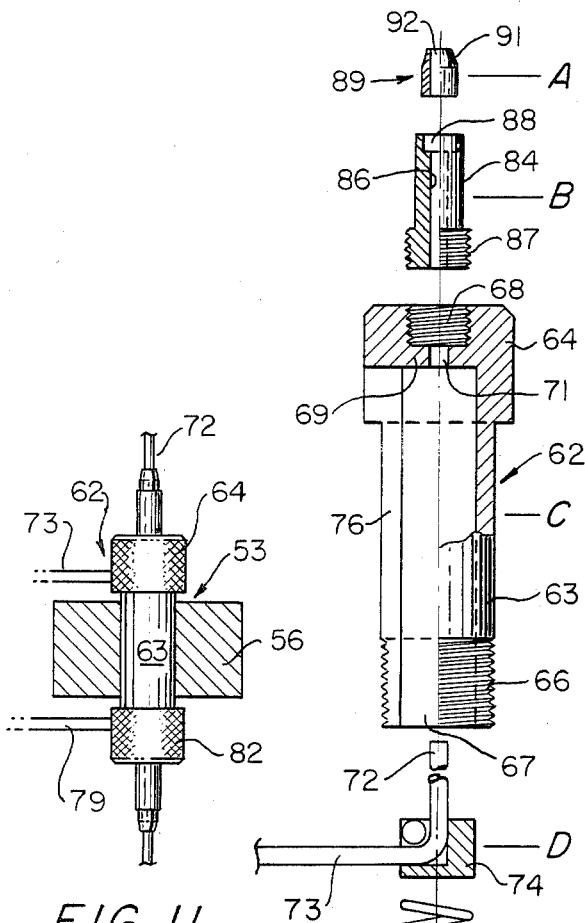
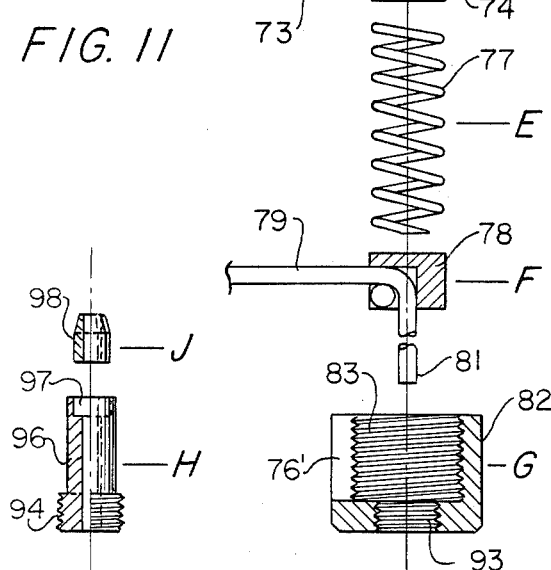
FIG. 11
FIGS. 12A-J
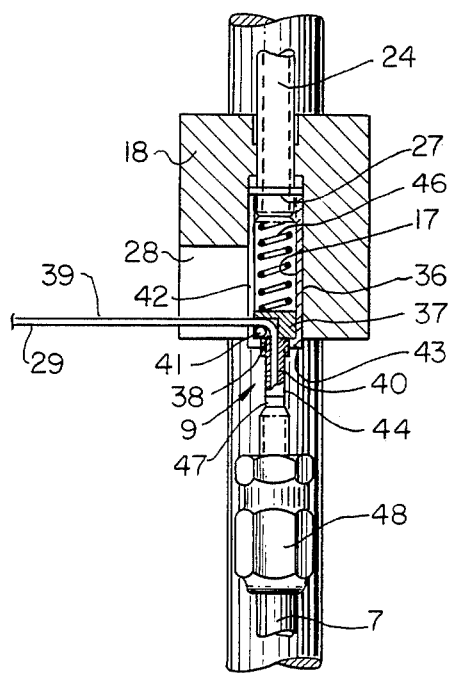
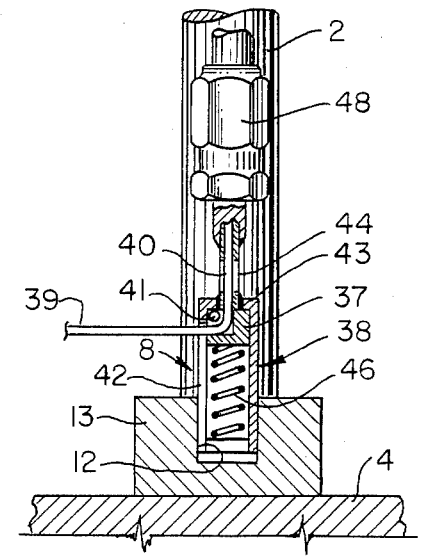
FIG. 13

UNIVERSALLY APPLICABLE MOUNTING APPARATUS FOR HIGH PRESSURE LIQUID CHROMATOGRAPHY COLUMNS

BACKGROUND OF THE INVENTION

1. Field of the Invention

This invention relates to supports and connecting apparatus for high pressure liquid chromatography (HPLC) columns and more particularly to a column support and connector apparatus adapted to facilitate the rapid mounting, release and interchange of columns in the apparatus.

2. Description of the Prior Art

The prior art related to this invention is believed to reside in Class 210, sub-class 198.

A preliminary patentability search through this area has indicated the existence of the following U.S. Pat. Nos. 3,266,554; 3,878,099; 3,531,919; 4,079,009; 4,288,007; 4,650,595; 4,440,550; 4,478,715.

While all of the patents noted above relate to chromatography devices, perhaps the most pertinent of the patents is U.S. Pat. No. 4,478,715 which discloses a column retainer and connector to other fluid flow members involving a split collet and collet nut for tightening onto the outside of a chromatography column. However, such a device is hardly applicable to the HPLC columns considered herein as these have specially designed end-fittings or column-connection unions applied to the highly-polished stainless steel tubes at the time the columns are packed with appropriate chromatographic packing materials.

A major problem in working with conventional HPLC columns has been that columns made by different manufacturers have different end-fittings, with different depths of ferrule seats and tube stops, thereby imposing a severe restriction on the user with respect to the variety of columns usefully accessible, it being generally not possible to change the style of end-fitting on a prepacked column. Accordingly, it is one of the objects of the present invention to provide an HPLC mounting station or apparatus which has universal sealing applicability and which can accommodate columns from different manufacturers.

A further object of the invention is to minimize or reduce to zero the fluid dead volume of the connections between the station and HPLC columns, the fluid dead volume being the fluid space between the input end of the fluid feed line, which has a generally micro-sized bore, and the surface of the packing materials in the HPLC column. This object is of particular significance since column end-fittings from different manufacturers may be either of the 'low dead volume' (LDV) or 'zero dead volume' (ZDV) design.

The high pressures employed in HPLC systems require that particular attention be given to the seals between the various components of the system. Accordingly, another object of the invention is to provide pressure seals between the station and HPLC columns which neither leak externally, nor permit internal leakage between components of the fluid system itself.

Conventional practice of liquid chromatography utilizing conventional HPLC columns, for best performance, dictates that each column should have a custom-made connecting tube. In general, to effect such custom-made connections, it is standard practice to have available an assortment of nuts, ferrules, and connecting tubes. This is particularly true where a conventional precolumn or in-line filter is used. Accordingly, it is another object of the invention to provide an apparatus that eliminates the need of all these extra nuts, ferrules and the tools required for their connection.

Still another object of the invention is the provision of a HPLC column mounting apparatus or station which provides for the convenient mounting of a sample injector as close to the column inlet as is feasible, to reduce to a minimum the delay, dilution, and detrimental band spreading effects due to mixing associated with introducing a sample onto the HPLC column.

Conventional HPLC columns are expensive components, and are susceptible to being contaminated and rendered useless after only limited use if care is not used regarding the purity of the solvent or fluid phase caused to pass through the column. It is conventional practice, to lessen the risk of such contamination, to utilize a precolumn or in-line filter to initially separate from the solvent any contaminants or impurities. Such filters cost much less than the columns, and significantly increase the life of the column, and assist in maintaining the efficiency of the column. The major problem encountered with use of such precolumn or in-line filters is the necessity of the additional liquid tight connections, the need to use tools to make those connections, and the expenditure of considerable time to effect the connections. Accordingly, it is a still further object of the invention to provide an apparatus for supporting and sealingly connecting a HPLC column and a precolumn or in-line filter in series with each other without the use of tools of any kind and solely by the application of axially directed mechanical pressure on the filter and column.

The invention possesses other objects and features of advantage, some of which, with the foregoing, will be apparent from the following description and the drawings. It is to be understood however that the invention is not limited to the embodiment illustrated and described, since it may be embodied in various forms within the scope of the appended claims.

SUMMARY OF THE INVENTION

The present invention provides an apparatus or station for quickly mounting and demounting high pressure liquid chromatography columns having a variety of unions, either male or female, at each end.

This is accomplished by providing a means for aligning an upper connector and a lower connector forming a permanent part of the station with the opposite axially aligned ends of the column, each connector being comprised of a connector housing in which is slidably mounted a connector assembly. Alignment is achieved by slidably mounting each connector housing on a rod having a longitudinal groove for accepting an aligning member associated with each connector housing. Because the connector housings are mounted on the same rod, columns of varying length may be accommodated and held in alignment by locking means associated with each connector housing, whereby the connector housings are locked in aligned orientation or position on the rod.

Sealing engagement between the station and each opposite end of a chromatography column occurs through connector assemblies, which provide the means for sealingly engaging either male or female unions on the column. The means for sealing engagement provides means for reducing to a minimum or providing a dead volume to the connection, and also provides means for sealing the connection between the station and the column fluid-tight even under pressures in the order of 6000 to 10,000 pounds per square inch of fluid pressure. The previously mentioned locking means associated with each connector housing also provides the locking means for maintaining the connector assemblies in sealing engagement with the unions of the column even at the high pressures indicated.

In order to maintain the dead volume of the connection, the connector assembly provides means for biasing a solvent line in the connector assembly against a tubing stop in the column union or on the end of the column per se.

Leakage between the station connector and column union, or between the station connector and the associated precolumn or in-line filter when one is used, and between the filter and column, is prevented by applying uniform axially directed pressure to the upper and lower seal connections and any intermediate connections. This pressure is supplied by a means for mutually urging the upper and lower connector assemblies toward each other and into compressed sealing engagement with the column. This urging means moves the upper connector assembly toward the column, relative to the connector housing which is locked in place on the aligning rod, thereby sealingly compressing both upper and lower and any intermediate seals into fluid-tight engagement.

To minimize dilution of a sample introduced onto the column through a sample injector, and to avoid detrimental band spreading effects due to mixing, means are provided for securing a sample injector in close proximity to the lower connector sealingly attached to the column so as to make this connection as short as possible.

In the preferred embodiment illustrated, a dual auxiliary connector adaptor also mounted on the rod is utilized to sealingly mount, without the need for tools of any kind, a precolumn or in-line filter in the fluid circuit in aligned orientation with the upper and lower connector housings.

BRIEF DESCRIPTION OF THE DRAWINGS

FIG. 7 is a fragmentary view in section illustrating a standard form of conventional union used with HPLC columns, shown apart from a column.

FIG. 8 is a fragmentary view in section of a low dead volume form of conventional union for HPLC columns, shown apart from a column.

FIG. 9 is a fragmentary view in section of a zero dead volume form of conventional union for HPLC columns, shown apart from a column.

FIG. 10 is a fragmentary view in section of a low dead volume inverted or male nut form of conventional union for HPLC columns, shown apart from a column.

FIG. 11 is an elevational view partly in section, of the auxiliary dual connector adaptor assembly for connecting a precolumn or in-line filter into the fluid circuit that includes a HPLC column.

FIGS. 12A through 12J illustrate in axially exploded form and partly in vertical section, the dual auxiliary connector adaptor assembly illustrated in FIG. 11.

FIG. 13 is an elevational view similar to FIG. 6, but with the dual auxiliary connector adaptor and precolumn filter removed and the HPLC column mounted directly between the apparatus connectors.

DESCRIPTION OF THE PREFERRED EMBODIMENT

Figure 1:
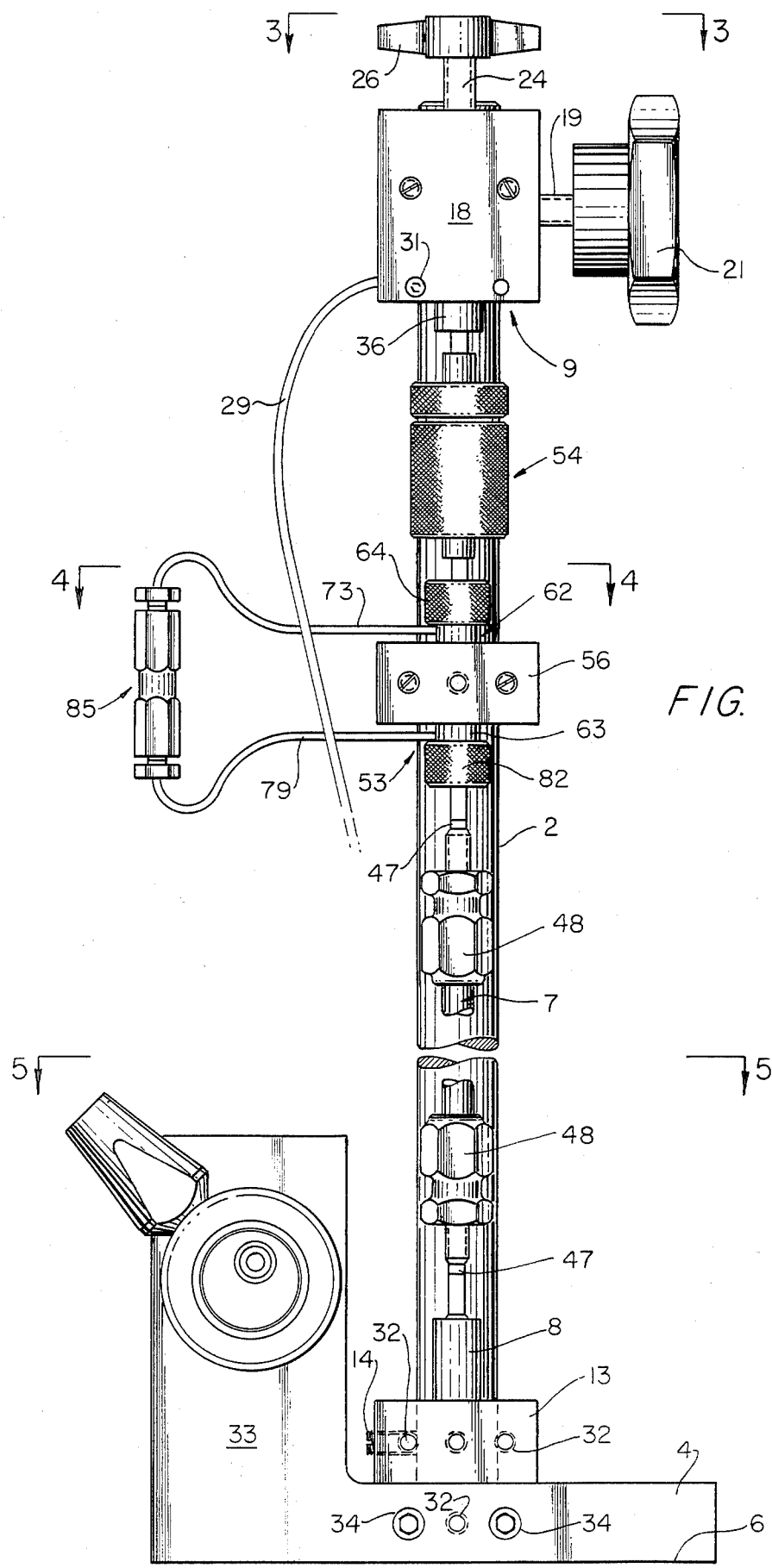
FIG. 1 is a front elevational view of the preferred embodiment of the apparatus of our invention in its assembled form, a portion of the structure being broken away to shorten the view.

In greater detail, our apparatus is illustrated and described in conjunction with a precolumn or in-line filter of conventional design, held in axial alignment and in series sealed connection with a conventional column through use of a novel and inventive dual auxiliary connector adaptor. It is of course obvious that while this is the preferred arrangement, the apparatus may be sealingly connected directly to a column without the interposition of the filter and dual auxiliary connector adaptor.

As illustrated, the apparatus or station includes an elongated supporting rod, designated 2 in the accompanying drawings and having a longitudinal generally V-shaped groove 3 extending the full length of the rod. The rod is preferably detachably mounted on a base plate 4, secured thereto in an upright or vertical attitude by a locking screw (not shown) passing through the underside 6 of the base plate and threadably engaging the end of the rod, which is drawn snugly into a bore formed in the base plate to form a seat for the end portion of the rod. Alternatively, the rod may be attached to an external laboratory framework by clamps which are not shown in the drawings. The base plate 4 is of such size as to provide lateral stability to the station when supported on a counter or table.

A high pressure liquid chromatography column 7 of conventional design is mounted on the station between spaced and axially aligned connector assemblies 8 and 9. The lower connector assembly 8 is snugly yet slidably mounted in a bore 12 formed in a lower connector housing 13 secured to the rod 2 by a locking screw 14 mediated by a ball 16 located in the longitudial groove 3. The locking screw and ball serve both to maintain the alignment of the lower connector assembly with the upper connector assembly 9, and prevent movement of the lower connector housing 13 with respect to the rod 2. The lower connector housing 13 is mounted at the base of the rod and in contact with the base plate 4, when the base plate is employed. In the absence of the base plate, as when the station is mounted on a wall by suitable clamps (not shown) the locking screw and ball lock the lower housing at any selected position along the rod.

The upper connector assembly 9 is slidably mounted in a bore 17 formed in the upper connector housing 18, the upper connector housing being slidably arranged on the rod for selective adjustment therealong, and selectively releasably secured to the rod 2 by a locking screw 19 mounted on the housing and having a knob 21 and soft silver alloy tip 22. The knob on the locking screw 19 permits rapid adjustment of the position of the upper connector housing 18 when mounting or changing a chromatography column, the relatively soft tip 22 providing a secure grip on the rod 2 without causing damage to its smooth surface. The upper connector housing 18 is maintained in alignment and proper orientation on the rod 2 with the lower connector housing by an aligning screw 23, the tip of which extends into the groove 3 sufficient to maintain the alignment and orientation of the housing 18 without interfering with the easy vertical movement of the housing 18 on the rod necessary for positional adjustments to accommodate a longer or shorter column, or for the interposition of a precolumn or in-line filter in series with the column. It will thus be apparent that the bores 12 and 17 are so positioned in their respective connector housings 13 and 18 that they are in coaxial alignment when the connector housings are secured in alignment on the rod 2. As a consequence, the connector assemblies 8 and 9 are similarly coaxially aligned and spaced when they are positioned in their respective bores 12 and 17.

A compressing screw 24 having a knob 26 and tip 27 is threadably mounted in the upper connector housing coaxial with the bore 17 therein, and is adapted to project into the bore 17 upon being tightened by turning the knob 26. This compressing screw is thus able to exert downward directed pressure through its tip 27 on the connector assembly 9 mounted in the bore 17, and provides the means whereby pressure is applied to the contact point between the connector assemblies and the chromatography column 7 to ensure a fluid-tight connection therebetween.

A transverse slot 28 in the upper connector housing 18 bisects the bore 17 and provides access for a rigid solvent line 29 to the connector assembly 9 from either side of the upper connector housing. A retaining screw 31 in the housing traversing the slot 28 acts to retain the connector assembly 9 in bore 17 by contacting the underside of the solvent line 29.

Screw holes 32 in the base plate 4 and lower connector housing 13 provide a means for detachably securing a sample injector mounting bracket 33 with locking screws 34. When a base plate is utilized, the bracket 33 is detachably secured to the base plate. Alternatively, when the base plate is not used, the bracket 33 is detachably secured to the lower connector housing, also provided with appropriate screw holes as shown.

The connector assemblies 8 and 9 are identical in construction and are interchangeable, and the description which follows applies to both. A tubular assembly sleeve 36 having open rearward and forward internally-threaded ends provides an inner bore in which is slidably mounted a cylindrical tube retainer 37 having circumferential and radial slots which meet to provide an L-shaped cavity 38. A segment of a solvent line 29 bent to form an L-shaped tube portion 39 fits into the cavity 38, and is held in place therein by a press-fitted spherical ball 41. The tube portion 39 and cavity 38 match in such a way as to direct one leg 40 of the L-shaped tube portion 39 coaxially with respect to the assembly sleeve 36, while the remaining leg extends radially outwards through a longitudinal slot 42 provided for that purpose.

The slot 42 permits the cylindrical tube retainer 37 and the retained L-shaped tube portion 39 to move axially in relation to the assembly sleeve 36. The slot 42 is contiguous with the rearward open end of the assembly sleeve 36, the rearward end of the housing being closed by a threaded cap 43. A tubular ferrule holder 44, having a ferrule seat 45, is threaded into the internally-threaded forward open end of the assembly sleeve 36, and provides slidable passage for the coaxially-directed leg 40 of the L-shaped tube portion 39. Thrust on the cylindrical tube retainer 37, and hence on the L-shaped tube 39, is maintained by a coil spring 46 located within the sleeve 36 between the threaded cap 43 and the cylindrical tube retainer 37. A plastic polymeric ferrule 47 seated in the end of the ferrule holder 44 provides an initially slidable snug passageway for the leg 40 of tube portion 39.

In its normal uncompressed state, the cylindrical tube retainer 37 is pushed by the coil spring 46 to the extreme forward end of the assembly sleeve 36 and the leg 40 of tube portion 39 extends through and beyond the ferrule 47 its maximum distance, sufficient to reach the tube stop 49 of either a male or female union 48 of the 'low dead volume' design on a chromatography column 7. In this position the plastic elastically deformable ferrule 47 does not yet make contact with the union 48. This is the condition which obtains when a chromatography column 7 is first introduced onto the lower connector assembly 8 of the station. By adjusting the position of the upper connector housing 18 on the upright rod, with the lower connector housing 13 locked in position, the upper connector assembly 9 is similarly placed in contact with the upper union 48 of the column. This condition exists, of course, when the column is mounted directly in the apparatus or station and in the absence of a precolumn or in-line filter in the fluid circuit. Assuming this condition, downward pressure on the upper connector housing 18 exerted by hand and with the lock screw 19 released, produces a reverse thrust in each of the legs 40 of the assembly housing tube portions 39, from the associated unyielding tube stops 49 in each of the column unions 48, resulting in compression of the connector assembly coil springs 46. This compression reaches a maximum limit when the ferrules 47 associated with each assembly sleeve 36 contact the generally conical seal seat 51 of the column unions 48. At this stage in the column mounting procedure, the upper connector housing 18 is locked in position on the rod by manipulating the locking screw 19. It should be clearly understood that at this stage in the mounting procedure, the ferrules physically contact the seats 51 but have not been deformed into sealing condition. Additional pressure, sufficient to completely seal the ferrules 47 against the union seal seats 51, is applied by tightening down the compressing screw 26 on the upper connector housing 18. This same additional pressure also serves to compress and seal the ferrules 47 against the walls of the legs 40 of tubes 39 by appropriate deformation of the ferrule. The compressed ferrules thus prevent leakage around the outer periphery of the ferrule, i.e., between the ferrule and the seats 51, and between the inner peripheries of the ferrules and the outer peripheries of the axially projecting legs 40 of tube portions 39.

With the ends of legs 40 of tube portions 39 remaining pressed in contact with the union tube stops 49 by the thrust of the coil springs 46, and the ferrules 47 pressure sealed against the union seal seats 51 and the tube 39, a condition of minimum dead fluid volume and complete sealing against leaks is achieved. This sealed condition is achieved solely by the application of axially directed pressure on the connector assemblies, which is accomplished without use of tools or threaded tube connections. When the column unions are of the 'zero dead volume' design the tubes 39 remain fully extended in the unions 52, coming into contact with the associated end of the column per se and thus maintaining the zero dead fluid volume condition.

While the description above relates primarily to the interconnection of a HPLC column directly in the apparatus or station as illustrated in FIG. 13, we have found that the preferred embodiment is that illustrated in FIGS. 1–6 wherein an auxiliary dual connector adaptor designated generally by the numeral 53 is utilized with the basic apparatus illustrated in FIG. 13 to mount in the fluid circuit in axial alignment with the column, a precolumn or in-line filter of conventional design and designated generally by the numeral 54.

Figure 2:
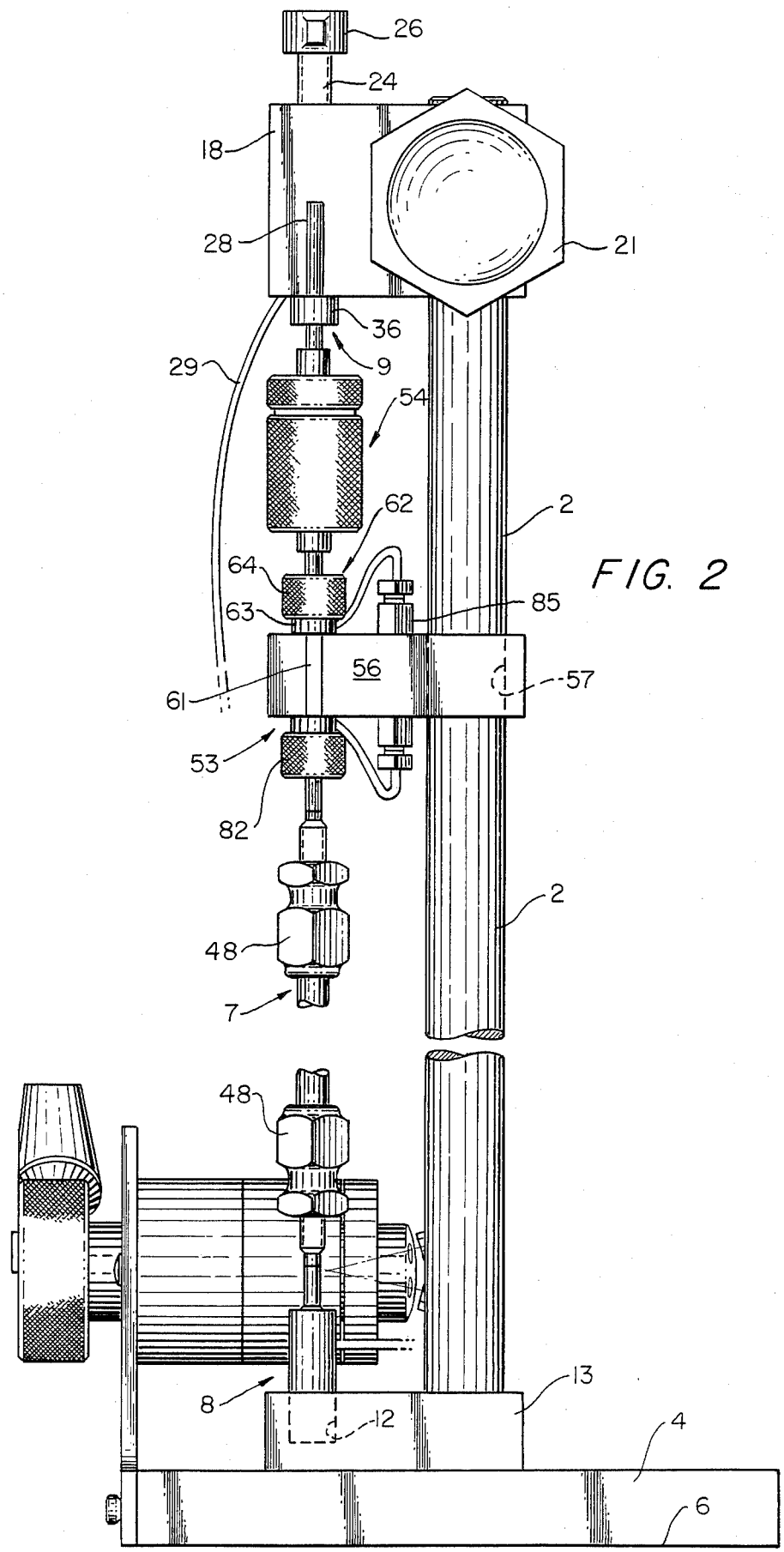
FIG. 2 is a side elevational view of the right side of the assembled apparatus illustrated in FIG. 1, a portion of the structure being broken away to shorten the view.
Figure 3:
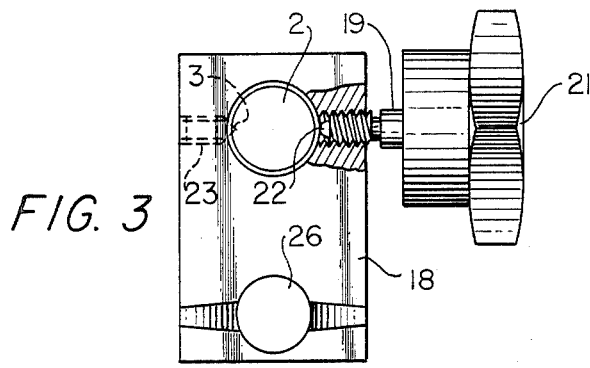
FIG. 3 is a top plan view of the upper connector of the apparatus apart from other structure, the view being taken in the direction of the arrows 3—3 in FIG. 1.
Figure 4:
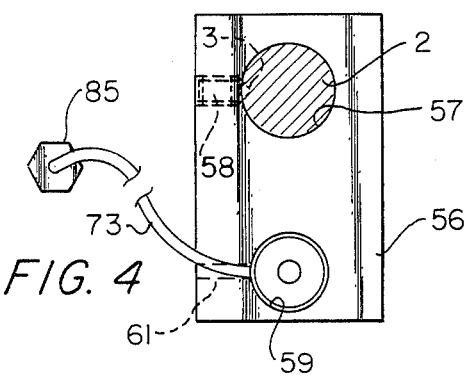
FIG. 4 is a horizontal cross-sectional view taken in the plane indicated by the line 4—4 in FIG. 1. The base and sample injector mechanism are omitted from this view for clarity.
Figure 5:
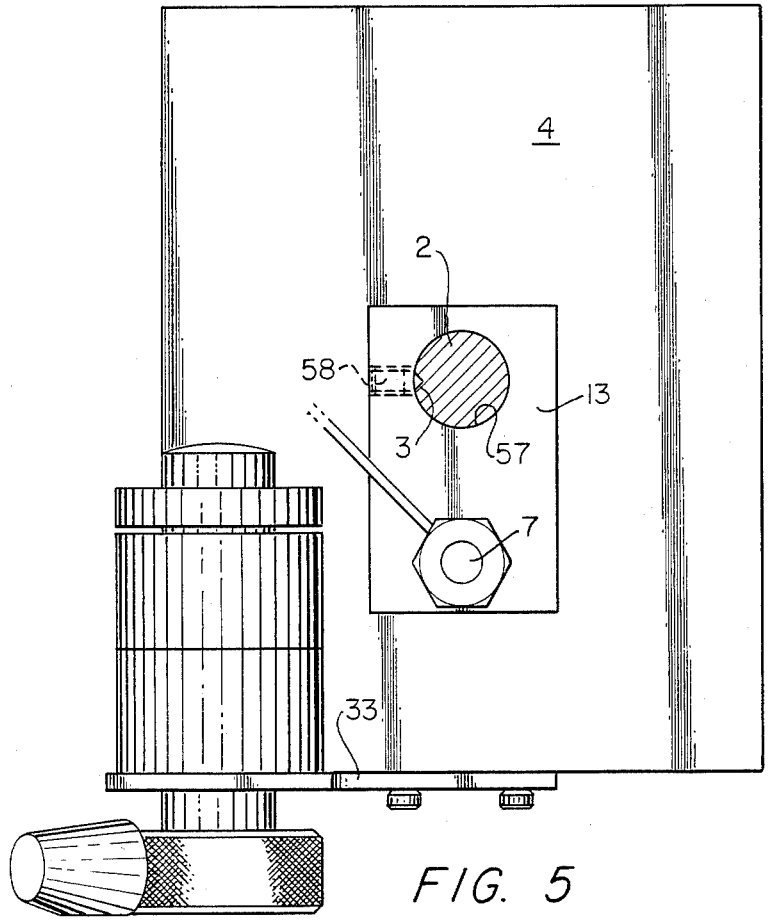
FIG. 5 is a horizontal cross-sectional view taken in the plane indicated by the line 5—5 in FIG. 1.
Figure 6:
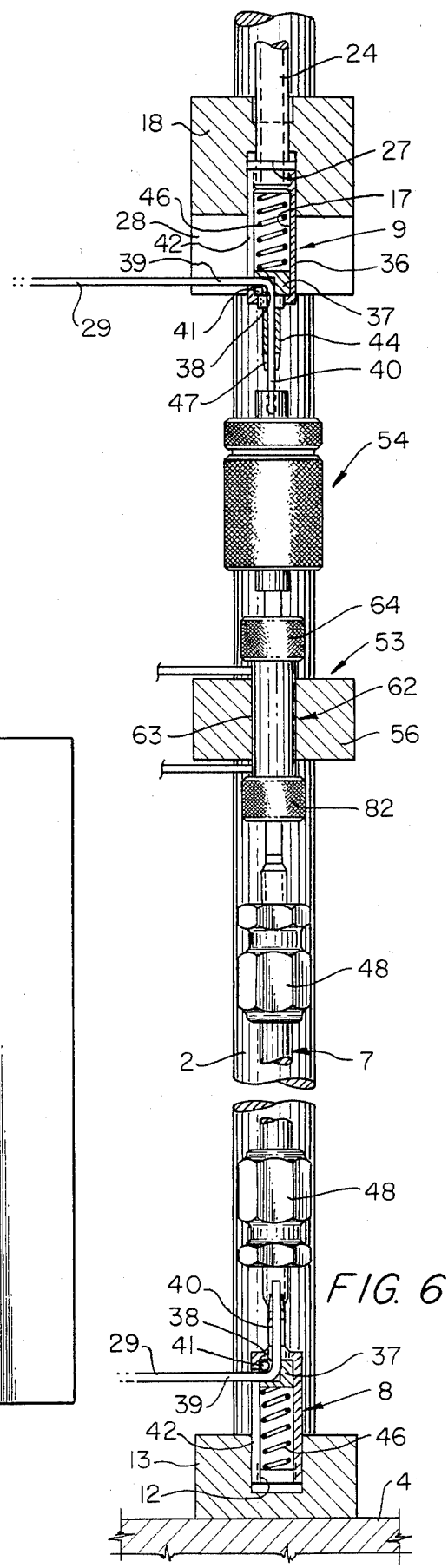
FIG. 6 is a front elevational view similar to FIG. 1, but with portions of the structure shown in section to show underlying structure.

Referring to FIGS. 1, 2 and 6, the HPLC column 7 is mounted over the upwardly projecting leg 40 of tube portion 39, with the end portion of the leg projecting into the column union as shown. Next, the auxiliary dual connector adaptor is slipped over the rod 2 and slid downwardly until the projecting auxiliary connector assembly engages the upper end of the HPLC column. As illustrated in FIGS. 1, 2 and 4, the auxiliary dual connector adaptor includes a rectangular body 56 having a bore 57 therethrough adapted to slidably receive the rod 2. A pointed set screw 58 threaded into the body projects into the groove 3 in the rod to orient the adaptor body and prevent rotation of the adaptor on the rod. The adaptor body 56 is provided also with a bore 59 parallel to the bore 57, and a transverse slot 61 that interesects one wall of the bore 59, the slot facilitating assembly of the adaptor prior to its use in conjunction with the column and filter, and providing some flexibility of the flange separated from the body of the adaptor by the slot so as to permit clamping pressure to be placed on the flange.

Slidably mounted in the bore 59 of the auxiliary dual connector adaptor is an elongated dual connector assembly designated generally by the numeral 62, and illustrated in greater detail in FIGS. 12A through 12J. As there shown, the dual connector assembly comprises an elongated cylindrical sleeve 63 having a head 64 at one end and external threads 66 at its opposite open end 67. The head 64 is counterbored to provide an internally threaded recess 68 closed at its bottom end by a transverse wall 69 having a central bore 71 sized to snugly receive the terminal end portion 72 of a solvent tube 73 bent at a right angle as shown and having secured at the bend a retainer member 74, as previously discussed, adapted to fit snugly and slidably within the elongated sleeve 63.

The sleeve 63 is provided with an elongated slot 76 in one side that extends from the open end 67 upwardly and into the head 64 as shown. When the retainer 74 is inserted into the sleeve 63, the slot accommodates the tube 73, which projects laterally outwardly as shown. Next, a coil spring 77 is slipped into the sleeve under the retainer 74, and a second retainer 78 mounted on tube 79 having a downwardly extending terminal end portion or leg 81, is inserted into the open end of the sleeve below the spring. It should be noted that the tube 79 is also accommodated by the slot 76 and is connected to the tube 73 by a coupling member 85 to complete the fluid circuit through the adaptor, column and filter; and the entire sub-assembly of tubes 73 and 79, retainers 74 and 78 and spring 77 is retained within the sleeve by an end cap 82 having internal threads 83 adapted to engage threads 66 on the sleeve. A slot 76' is provided in one wall of the end cap 82 and aligns itself as a continuation of slot 76 when the end cap "bottoms" on the threaded sleeve.

It will thus be seen that because of the interposition of the spring 77, there is a measure of axial adjustment of the retainers 74 and 78 within the sleeve 63. Since the terminal end portions 72 and 81 of the tubes 73 and 79 are connected to the respectively associated retainers 74 and 78, these terminal end portions are also axially displaceable toward and away from each other within prescribed limits imposed by total compression of the spring 77 on the one hand, and by the head 64 at one end and the end cap 82 on the opposite end and the length of the cavity within the sleeve. This range of positional adjustment of the terminal end portions of the tubes is important as will hereinafter be explained.

Detachably mounted on the head 64, specifically, threadably engaged in recess 68, is a tubular ferrule support member 84, having a central bore 86 adapted to snugly and slidably receive the terminal end portion 72. At one end the tubular ferrule support member is provided with external threads 87 adapted to engage the internal threads of the recess 68. At its opposite end, the tubular ferrule support member is counterbored to provide a cylindrical recess 88 adapted to snugly receive the cylindrical base end of the polymeric elastically deformable ferrule 89, the opposite end 91 of which is tapered as illustrated. The ferrule is provided with a central bore 92 sized to snugly and slidably receive the outer periphery of the terminal end portion 72 of the tube 73. These components are sized such that at all times the extreme free end of the terminal portion 72 projects sufficiently beyond the tapered end of the ferrule so as to seat against the tube stop provided in the low dead volume unions illustrated in FIGS. 7, 8 and 10, or to project sufficiently through the zero dead volume union of FIG. 9 so that the extreme end of the tube extension 72 seats on the end of the column per se. In this regard, these columns are provided with an apertured end plate (not shown), and the end of the tube extension 72 impinges against the end plate so that the microbore of the tube is axially aligned with the aperture in the plate, which is usually considerably larger than the microbore in the tube.

At the opposite end of the assembly as illustrated in FIGS. 12F through 12H, the end cap 82 is provided with an internally threaded bore 93 adapted to receive the threaded end 94 of the associated tubular ferrule support member 96 which is of similar construction as the ferrule support member 84, and which provides a seat 97 for the polymeric elastically deformable ferrule 98 which is of similar construction as the ferrule 89.

It will thus be seen that the interconnection of a HPLC column with a source of high pressure solvent and a sample injector mechanism is a simple and quick process. In like manner, the removal of a HPLC column is simple and quick, both procedures being accomplished without the use of tools of any kind, while the seals completed between the apparatus and the column are fluid tight to pressures in excess of 6000 pounds per square inch.

Referring to the basic apparatus illustrated in FIG. 13, it will be seen that to mount a HPLC column 7 in the apparatus, all that is required is that the lower end of the column be fitted over the projecting leg 40 of the lower connector assembly while the column is held generally parallel to the rod 2. With the column so held, the upper connector knob 19 is loosened sufficiently to permit the upper connector to descend until the upper connector terminal tube portion that projects through the upper ferrule enters the end of the column union and seats against the tube stop. In this position of the parts, the ferrules of the upper and lower connector assemblies have still not come in contact with the column unions, but the two projecting terminal ends of the feed tubes are seated either against the tube stops in the case of low dead volume unions, or against the end plates of the column per se in the case of the zero dead volume column unions.

Now, with the lock screw 19 still loose, hand pressure is applied to the upper connector housing in a downward direction until the ferrules seat in the respective ends of the column unions. In this regard, and referring to FIG. 6, it should be noted that this downward pressure on the upper connector housing results in downward displacement of the upper connector assembly sleeve in relation to the tube which projects laterally through the slot in the sleeve, thus causing compression of the spring and downward displacement of the ferrule holder and ferrule in relation to the terminal end portion of the tube which they surround, until the ferrules seat firmly but not sealingly at this time against the seats 51 on the column unions. The screw 19 is now tightened against the rod 2 to lock the upper connector housing to the rod against longitudinal displacement. Next, to secure positive sealing of the ferrules in the seats 51 by elastic deformation of the ferrules to conform sealingly to the seats 51 and to the outer periphery of the associated terminal end portions of the solvent feed tubes, the connector assembly compressing screw 24 in the upper connector housing is tightened to drive the associated connector assembly sleeve 36 in the upper connector housing downwardly, completely compressing the spring, and thus converting the spring into a ram impinging upon the associated cylindrical tube retainer, thus preventing separation of the extreme end of the terminal end portion of the tube from the tube stop in the column union, or from the end plate in the column, whichever the case may be, while the sleeve 36 continues downwardly under the impetus of the screw 24, displacing the ferrule holder 44 downwardly to compress the ferrules 47 into their respective seats 51 with such force that the ferrules elastically deform to tightly occupy the seats and permit no space to exist between the ferrules and the seats, nor between the ferrules and the outer peripheries of the associated terminal end portions of the feed tubes.

With the column thus sealingly locked to the apparatus to complete the fluid circuit, a sample of the fluid to be separated is injected with an appropriate hypodermic-type device into the sample injector mechanism mounted on the bracket 33, and the injector control lever is manipulated to inject the sample into the fluid circuit.

The foregoing explains the procedure for mounting a HPLC column in the apparatus of our invention without the intervention of a precolumn or in-line filter, this arrangement being shown in FIG. 13.

The procedure for mounting a HPLC column in the apparatus in conjunction with a precolumn or in-line filter 54 as illustrated in FIGS. 1, 2 and 6 is very similar to the procedure outlined above, but with the added steps of placement of the auxiliary dual connector adaptor on the rod so that the dual auxiliary connector assemblies are axially aligned with the upper and lower connector assemblies mounted in the upper and lower connector housings. This is accomplished simply by engaging the point of the set screw 58 in the groove 3 of the rod 2. With the auxiliary dual connector adaptor slidably mounted on the support rod 2, the HPLC column is mounted on the lower connector assembly as before, and the lower auxiliary connector assembly of the auxiliary dual connector adaptor is brought into engagement with the upper end union of the column. When this is done, the column will support the weight of the auxiliary dual connector adaptor and the column will be retained in parallel relation to the support tube 2. Additionally, the terminal end portions of the feed tubes of the connector assemblies will have bottomed on the associated tube stops of the column, but the associated ferrules will not yet be in contact with the associated union seats.

Next, the precolumn or in-line filter 54 is placed in alignment with the upper auxiliary connector assembly so that the upper terminal end portion 72 of the feed tube 73 seats in the lower tube stop of the filter member 54. Then, while the filter member is held in substantial alignment with the upper connector assembly, the upper connector housing is lowered by loosening the screw 19, causing the connector housing to descend until the terminal end portion of the upper connector assembly enters the opposite end of the filter member and seats or abuts the tube stop associated therewith. The procedure is thereafter similar to that described previously, with downward pressure by hand being applied on the upper connector housing to displace it downwardly to load the springs and bring the ferrules into engagement, albeit not sealing engagement, with the associated seats in the column and in the filter member. The screw 19 is then tightened to lock the upper connector housing to the rod 2, and the compressing screw 24 is manipulated to impose a downwardly directed pressure on the sleeve 36 as before, with the result that all of the four ferrules are elastically deformed into tight sealing engagement with their associated seats.

While we have described the apparatus as mounted as an independent upright unit on a counter top or table, or clamped to a wall, it is contemplated that the apparatus may be mounted horizontally or at any convenient angle. Thus, while we have referred spacially to some components as being "upper" or "lower", these could as well be "left" or "right" as the circumstances dictate.

Although the invention has been described above by reference to a preferred embodiment, it will be appreciated that other constructions may be devised, which are, nevertheless, within the scope and spirit of the invention as defined in the appended claims and sought to be protected by letters patent of the United States as follows.

We claim:

1. An apparatus enabling without use of tools, the quick and universal connection and disconnection of a high pressure chromatography column to a source of solvent under high pressure and an injector mechanism for injecting a sample of fluid to be analyzed into the solvent stream, comprising:

(a) an upper connector;

(b) a lower connector, wherein each said connector includes:

(i) a connector housing; and
(ii) a connector assembly slidably mounted in said connector housing;
(c) means for aligning and supporting said upper and lower connectors, wherein said means for aligning said upper and lower connectors includes:
(i) an elongated rod;
(ii) upper and lower connector housings mounted on said rod and having a bore therein parallel to said rod; and
(iii) an aligning member on each housing adapted to engage said rod, whereby said housings are retained in longitudinal alignment and the bores therein are retained in coaxial alignment;
(d) means for engaging said upper connector with one end of the column and said lower connector with the other end of the column;
(e) means for locking said upper and lower connectors in engagement with the column; and
(f) means for mutually urging said upper and lower connectors toward each other and into sealed engagement with the column.

2. An apparatus as described in claim 1, wherein said means for engaging opposite ends of said column includes a connector assembly having:
(a) a connector assembly housing;
(b) a tubular ferrule holder demountably secured to said connector assembly housing; and
(c) a deformable plastic ferrule seated in said ferrule holder for making sealing contact with the associated end of the column.

3. An apparatus as described in claim 2, wherein said means for mutually urging said upper and lower connectors toward each other comprises a compressing screw mounted in cooperative association with said upper connector assembly whereby when said compressing screw is tightened said upper connector assembly is urged downwardly towards said lower connector assembly to deform said ferrules into compressed sealing engagement with the column.

4. An apparatus as described in claim 1, wherein said means for locking said connectors in engagement with the column comprises a locking screw mounted in cooperative association with each said connector such that said locking screw may be selectively tightened to prevent movement of said connector relative to said column.

5. An apparatus as described in claim 1, wherein an injector mounting bracket is provided for mounting a sample injector mechanism in close proximity to said column.

6. An apparatus as described in claim 5 wherein said injector mounting bracket is demountably attached to said lower connector housing.

7. An apparatus as described in claim 1, wherein a base plate is provided, and said rod is demountably attached to the base plate; and an injector mounting bracket is demountably attached to said base plate.

8. An apparatus as described in claim 1, wherein a locking screw having a soft silver alloy tip is provided in at least one of said connector housings manipulable to selectively lock the housing to said rod without marring the rod.

9. An apparatus as described in claim 1 wherein the aligning member of said upper connector housing comprises an aligning screw mounted transversely through the housing to thereby make contact with a longitudinal groove in said rod.

10. An apparatus as described in claim 1 wherein the aligning member of said lower connector housing comprises a ball in combination with a second locking screw mounted transversely through the housing to thereby position and selectively clamp said ball in a longitudinal groove of said rod.

11. An apparatus as described in claim 1, wherein said upper connector housing is provided with a transverse slot extending upwardly from the lower surface thereof coincident with the axis of said bore and bisecting the bore longitudinally for facilitating mounting of the connector assembly in said housing.

12. An apparatus as described in claim 1, wherein an auxiliary dual connector adaptor is operatively interposed in the solvent stream between said upper and lower connectors, and a precolumn filter is operatively interposed in the solvent stream between said auxiliary dual connector adaptor and a selected one of said upper and lower connectors.

13. The apparatus as described in claim 12, wherein said auxiliary dual connector adaptor is mounted on said means for aligning and supporting said upper and lower connectors.

14. The apparatus as described in claim 13, wherein said auxiliary dual connector adaptor comprises a main body, a pair of axially aligned auxiliary fluid connector assemblies mounted on said main body and connected so that fluid passes serially therethrough, and means on said fluid connector assemblies for sealingly engaging one end of said column on the one hand and sealingly engaging said precolumn filter on the other hand whereby solvent under pressure from said source flows serially through said filter, said auxiliary fluid connector assemblies and said column.

15. The apparatus as described in claim 14, wherein said pair of axially aligned auxiliary fluid connector assemblies include a tubular sleeve having a head at one end provided with a threaded recess constituting a seat and an elongated slot in one wall of the sleeve, a selectively detachable end cap closing the end of the sleeve remote from the head and providing a threaded recess constituting a seat, axially aligned ferrule holder members mounted in said threaded recesses and projecting in opposite directions from opposite ends of said sleeve, elastically deformable tubular ferrules mounted on said ferrule holder members on the ends thereof remote from said sleeve, a pair of tube retainer members slidably disposed within said sleeve, a coil spring within the sleeve disposed between said retainer members, and a section of solvent tube mounted on said tube retainers and an intermediate portion extending out of said slot in the sleeve while the opposite ends of said solvent tube section are axially aligned and project through opposite ends of the sleeve and the associated ferrule holder member and ferrule to provide a predetermined end portion of the solvent tube projecting from the associated ferrule.

16. A connector assembly for a high pressure liquid chromatography column, comprising:
(a) a tubular connector assembly sleeve having a slotted end and a non-slotted end, each end being open and internally threaded, said sleeve having a longitudinal slot extending from the slotted end to adjacent the non-slotted end;
(b) a threaded cap for closing the slotted end of said sleeve;
(c) a tubular ferrule holder having a threaded end for engaging the internal threads of the non-slotted end of said sleeve and a plain end formed with a ferrule seat for receiving a ferrule;

(d) a plastic elastically deformable ferrule mounted in said ferrule seat of the ferrule holder;

(e) an L-shaped tube having two legs, one leg slidably mounted in said ferrule holder and in said ferrule;

(f) a cylindrical tube retainer slidably mounted in said tubular sleeve, said retainer having a radial slot and a circumferential slot, the slots meeting to form an L-shaped cavity for mounting said L-shaped tube such that one leg of said tube is directed coaxially along said tubular sleeve toward the non-slotted end of said tubular sleeve, and the other leg of said tube is directed radially through said longitudinal tubular sleeve slot;

(g) a spherical ball press-fitted in the L-shaped cavity of said tube retainer after said L-shaped tube is inserted to retain said L-shaped tube associated with said slotted cylindrical retainer; and (h) a coil spring interposed between said threaded cap and said tube retainer for biasing said tube retainer toward said non-slotted end of the sleeve.

17. A device for connecting without the use of tools a high pressure liquid solvent line to a high pressure liquid chromatography column equipped with a union having a shoulder forming a tubing stop, comprising:

(a) means for maintaining the solvent line in position against the tubing stop of the column union, wherein said means for maintaining said solvent line position includes:

(i) a connector housing;

(ii) means maintaining said connector housing in fixed positional relation in relation to the column; and (iii) a connector assembly slidably mounted in said connector housing and adapted to operatively engage said column, and (b) means responsive to the application of mechanical pressure for sealing a gap between the solvent line and the column union.

18. The device as described in claim 17, in which said connector assembly includes an assembly sleeve, and a solvent line retainer slidably mounted in said assembly sleeve.

19. The device according to claim 18, in which said means responsive to the application of mechanical pressure for sealing the gap between the solvent line and the column union includes:

(a) a ferrule holder detachably secured to said assembly sleeve;

(b) a plastic elastically deformable ferrule mounted in said ferrule holder; and (c) means mounted on said connector housing for applying mechanical pressure on said connector assembly, whereby said connector assembly slidably responds to such pressure relative to said connector housing to thereby force said ferrule into sealing compression with the column union and said solvent tube.

* * * * *